United States Patent [19]

Webb

[11] Patent Number: 5,944,014
[45] Date of Patent: Aug. 31, 1999

[54] COLLECTION TRAY FOR USE IN PELVIC PROCEDURES AND IN PARTICULAR FOR USE IN VAGINAL DELIVERY AND EPISIOTOMY PROCEDURES

[75] Inventor: Nicholas J. Webb, Wrightwood, Calif.

[73] Assignee: Cetus, L.C., San Antonio, Tex.

[21] Appl. No.: 08/950,122

[22] Filed: Oct. 14, 1997

Related U.S. Application Data

[63] Continuation-in-part of application No. 08/762,196, Dec. 9, 1996, Pat. No. 5,792,125.

[51] Int. Cl.$^6$ ..................................................... A61G 15/00
[52] U.S. Cl. ............................................ 128/845; 128/846
[58] Field of Search .................................. 604/317, 356, 604/357; 4/144.1–144.4; 206/564, 570

[56] References Cited

U.S. PATENT DOCUMENTS

| | | | |
|---|---|---|---|
| 2,098,673 | 11/1937 | Pollock | 604/317 |
| 3,131,403 | 5/1964 | Hill | 604/317 |
| 3,249,070 | 5/1966 | Day | 604/356 |
| 3,386,444 | 6/1968 | Brenner et al. | 128/292 |
| 3,719,188 | 3/1973 | Fisher et al. | 128/275 |
| 4,007,741 | 2/1977 | Waldrop et al. | 128/292 |
| 4,024,590 | 5/1977 | Wendt | 4/166 |
| 4,076,017 | 2/1978 | Haswell | 128/2 |
| 4,105,019 | 8/1978 | Haswell | 128/2 |
| 4,149,537 | 4/1979 | Haswell | 128/292 |
| 4,503,864 | 3/1985 | Powers | 128/760 |
| 4,553,538 | 11/1985 | Rafelson | 128/132 |
| 4,905,710 | 3/1990 | Jones | 128/849 |
| 5,170,804 | 12/1992 | Glassman | 128/849 |
| 5,224,679 | 7/1993 | Code | 248/314 |
| 5,287,860 | 2/1994 | Owens | 128/851 |
| 5,392,469 | 2/1995 | Adams | 4/245 |
| 5,395,354 | 3/1995 | Vancaillie | 604/317 |
| 5,454,797 | 10/1995 | Haswell | 604/317 |
| 5,487,393 | 1/1996 | Haswell et al. | 128/760 |

*Primary Examiner*—Michael A. Brown
*Attorney, Agent, or Firm*—David P. Gordon; David S. Jacoboson; Thomas A. Gallagher

[57] ABSTRACT

A collection tray for use in pelvic procedures includes a single piece molded plastic tray having a planar portion, a basin portion, and a live hinge therebetween. The basin portion is preferably provided with a central drain which includes a sponge barrier. The basin portion is also provided with a shelf having one or more slots for holding an irrigation fluid tube so that irrigation fluid may be easily directed toward the site of the procedure. A pair of ears defining instrument receiving holes are preferably located adjacent to the basin portion and the live hinge.

16 Claims, 2 Drawing Sheets

COLLECTION TRAY FOR USE IN PELVIC PROCEDURES AND IN PARTICULAR FOR USE IN VAGINAL DELIVERY AND EPISIOTOMY PROCEDURES

This application is a continuation-in-part of application Ser. No. 08/762,196 filed Dec. 9, 1996, now U.S. Pat. No. 5,792,123, the complete disclosure of which is hereby incorporated by reference herein in its entirety.

BACKGROUND OF THE INVENTION

1. Field of the Invention

The present invention relates to a device for collecting fluids during pelvic procedures such as obstetric, gynecologic, proctologic or urologic procedures. More particularly, the invention relates to a molded disposable plastic tray having structure for collecting fluids and irrigating a surgical site.

2. State of the Art

During vaginal delivery and other types of pelvic procedures it is necessary to collect and drain fluids (and particles entrained in the fluids) which flow from pelvic tracts. The art discloses several devices for achieving this purpose.

U.S. Pat. No. 3,386,444 to Brenner et al. discloses a surgical drain bag and support for use in urological surgery. The drain bag has four flexible side walls, is shaped like an inverted pyramid, and is provided with a drain in a lower portion. The support includes a number of rods which are attached to the end of an examination table and which suspend the bag in a curtain-like manner. The bag also has a flap which rests against the practitioner's chest and acts as a splash guard. This drain bag is a vast improvement over the previously used drain drawers which impeded physician access to the surgical site. Nevertheless, it is cumbersome to install and relatively expensive to manufacture.

U.S. Pat. No. 4,007,741 to Waldrop et al. discloses a transurethral resection apron system which is similar in concept to the drain bag described above. The apron is somewhat simpler to mount, however. It is provided with four corner ties, two of which are tied to uprights on a urological table, and the other two of which are tied to each other behind the surgeon's neck. While this apron offers some advantages over the drain bag, it is still cumbersome to use and relatively expensive to manufacture. Moreover, the attachment to the surgeon's neck inhibits the surgeon and interferes with the surgical procedure.

U.S. Pat. Nos. 4,076,017, 4,105,019, and 4,149,537 to Haswell disclose various embodiments of a postpartum fluid loss receptacle. The receptacle is formed from a substantially rectangular sheet which is folded along its longitudinal axis such that one edge is folded upon itself and sealed to form a pouch. The open end of the sheet is positioned under the patient's buttocks and is thereby supported. The pouch may hang freely from the examination table, or may be supported in a bucket. While the receptacle is relatively inexpensive to manufacture and relatively easy to use, the pliant sheet material does not readily locate the pocket in a convenient manner. It is easy for the pocket to fill and spill over, or to be mispositioned.

U.S. Pat. No. 5,287,860 to Owens discloses a birthing drape. The drape has the geometry of an inverted top hat, with a distal flap and two proximal stirrups. The distal flap is positioned under the patient's buttocks and the stirrups are attached to the patient's ankles. While the drape has some advantages, it is relatively expensive to manufacture and the ankle support stirrups may result in instability of the drape and discomfort for the patient.

U.S. Pat. No. 5,454,797 to Haswell discloses a combined pelvic tray, work station, and fluid collection device. The tray is a rigid sheet of plastic or stainless steel having a first portion which is positioned under the patient's buttocks and a second portion which has a fluid receiving well, receptacles for solutions, instruments, and swabs. A raised fluid dam or dike separates the first and second portions and prevents fluids from flowing under the patient's buttocks. While the rigid plastic tray is easy to use and relatively inexpensive to manufacture, the dam is not completely effective, and the location of the proximal portion of the tray can obscure the surgical site. More specifically, the dam may simply direct the flow of fluids off the side of the tray onto the floor; and the location of the proximal portion of the tray prevents access to the surgical site from below the horizontal plane. In addition, the fluid receiving well is relatively small and is likely to fill quickly.

During vaginal deliveries, it is common to perform an episiotomy. This procedure releases relatively large quantities of blood which must be collected. The above-described devices are more or less successful in collecting blood during an episiotomy procedure. In addition to the need to collect blood during the episiotomy procedure, the flow of blood obscures the surgical site and it is necessary to irrigate the surgical site. The prior art of fluid collection devices does not address this need for irrigation during episiotomy procedures.

The parent application hereto discloses a collection tray for use in pelvic procedures which includes a single piece molded plastic tray having a planar portion, a basin portion, and a live hinge therebetween. The basin portion is preferably provided with a central drain which is adapted to be coupled to a vacuum line. The basin portion is preferably provided with one or more clip structures for holding an irrigation fluid tube so that irrigation fluid may be easily directed toward the site of the procedure. The tray is preferably manufactured by vacuum forming techniques and the outer edge of the basin portion is preferably rolled down to provide a smooth edge and enhanced structural support. A kit containing the tray includes a fluid collection system and an irrigation system having an articulatable nozzle.

Since the filing of the parent application, several improvements have been conceived regarding the central drain, the clip structures, the articulatable nozzle, as well as other aspects of the tray.

SUMMARY OF THE INVENTION

It is therefore an object of the invention to provide a collection tray for use in pelvic procedures which is easy to use and inexpensive to manufacture.

It is also an object of the invention to provide a collection tray for use in pelvic procedures which has a large collection region and a drain.

It is also a particular object of the invention to provide a collection tray which minimizes the risk of blood born or fluid born pathogens from contaminating health care workers.

It is another object of the invention to provide a collection tray for use in pelvic procedures which does not obscure the surgical site.

It is still another object of the invention to provide a collection tray for use in pelvic procedures which accommodates an irrigation tube for flushing the surgical site.

It is also an object of the invention to provide a collection tray with a controllable irrigation system.

It is another object of the invention to provide an apparatus for irrigating an episiotomy site while concurrently collecting vaginal fluids.

Yet another object of the invention is to provide an apparatus for irrigating an episiotomy site while concurrently collecting vaginal fluids which can be used in conjunction with a surgical drape.

Still another object of the invention is to provide an apparatus for irrigating an episiotomy site while concurrently collecting vaginal fluids in which sponges are not lost through the drain of the apparatus.

Another object of the invention to provide a collection tray for use in pelvic procedures which accommodates several instruments in addition to an irrigation tube.

In accord with these objects which will be discussed in detail below, the collection tray of the present invention includes a single piece plastic tray having a planar first portion, a second basin portion, and a live hinge therebetween. The planar first portion is preferably provided with adhesive strips for attaching the tray to a surgical drape. The basin portion is preferably provided with a central drain having a lower barrier which prevent sponges from passing therethrough. The basin portion is also preferably provided with a sloped ledge adjacent to the live hinge. The ledge is provided with three slots for receiving an irrigation tube in any of three different locations. A pair of planar portions (ears) are arranged adjacent to both the basin portion and the live hinge and are provided with instrument receiving holes for holding instruments during the procedure. A presently preferred irrigation fluid tube for use with the invention includes a spike for connection to a sterile water bottle, an inline valve for controlling the flow of water, and a luer coupling. An articulate nozzle for directing the flow of water to the surgical site is made of a malleable metallic tube having an inverted J shape extending from a luer coupling. The slots in the ledge of the basin portion are dimensioned to receive the luer coupling and a portion of the fluid tube adjacent to the luer coupling.

Preferred aspects of the invention include manufacturing the tray by vacuum forming techniques, and die cutting the outer edge of the basin portion to provide a smooth edge. The presently preferred material for manufacturing the tray is a medical grade gamma stable low density polyethylene such as PETG, polystyrene, or other similar material.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
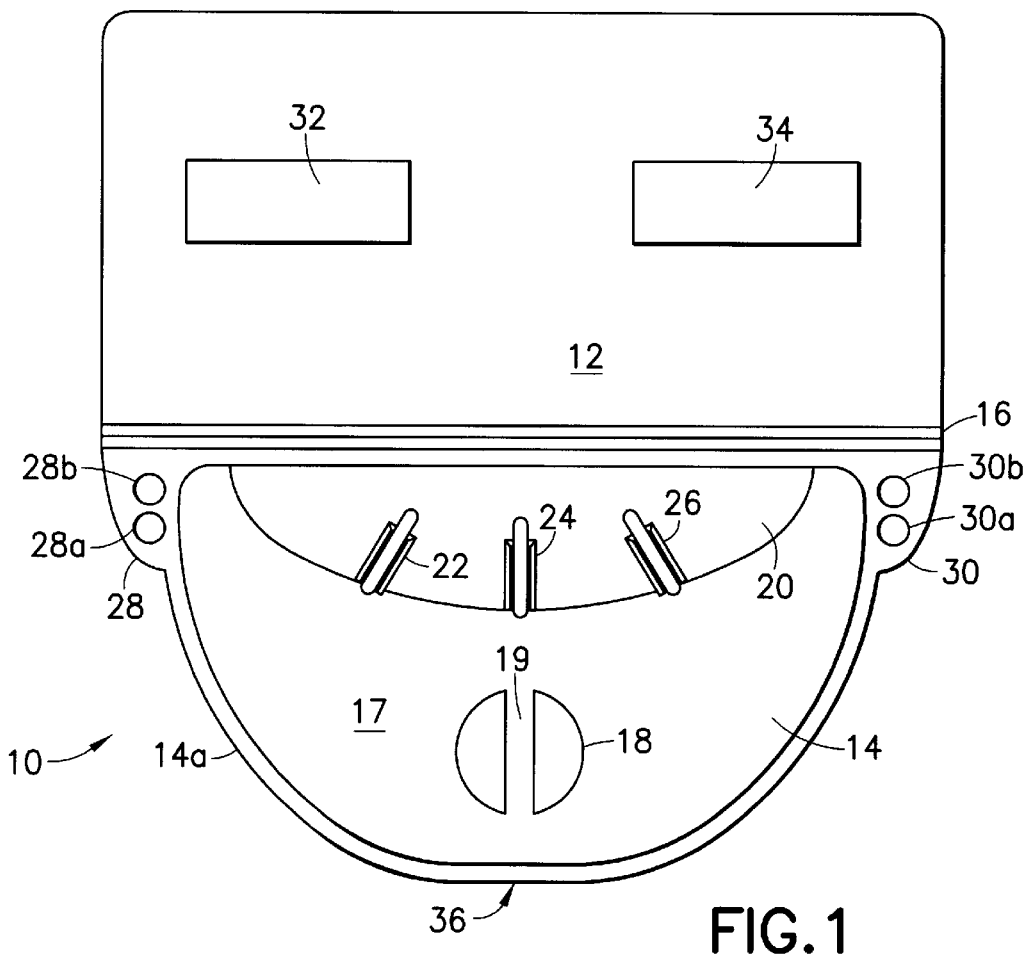
FIG. 1 is a top plan view of a presently preferred embodiment of the collection tray of the invention shown with an irrigation tube.
Figure 2:
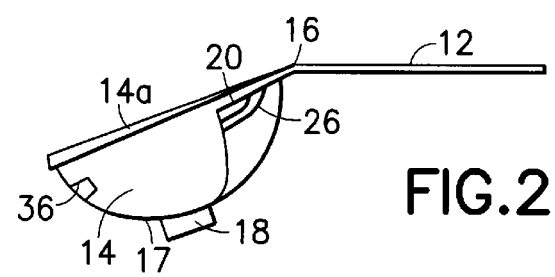
FIG. 2 is a side elevation view of the collection tray of FIG. 1 folded to a presently preferred configuration for use.
Figure 3:
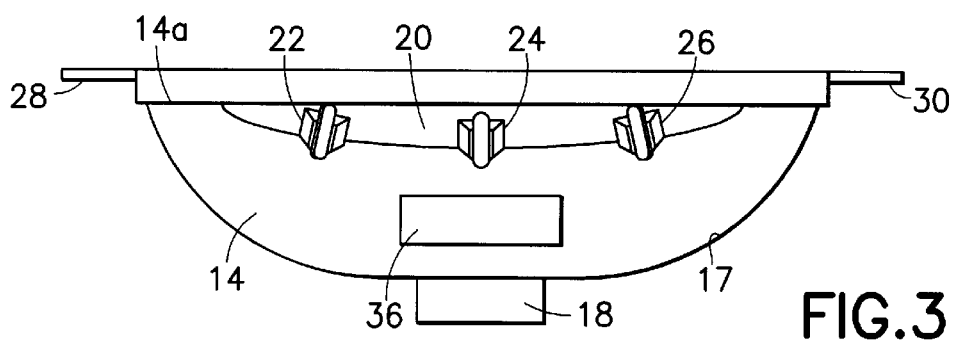
FIG. 3 is a proximal end elevation view of the tray of FIG. 1.
Figure 4:
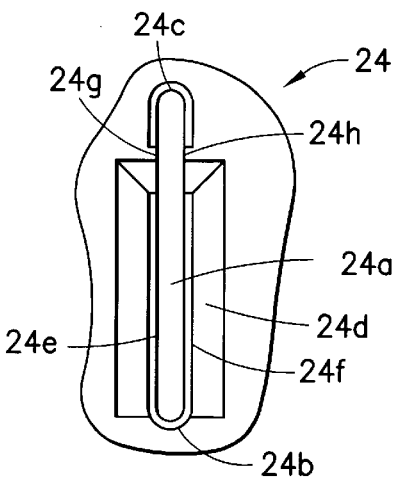
FIG. 4 is an enlarged schematic top view of one of the slots in the ledge of the tray.
Figure 5:
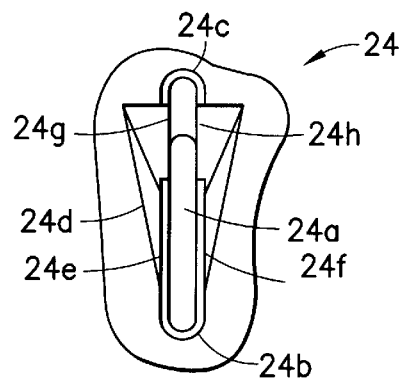
FIG. 5 is an enlarged schematic proximal end view of one of the slots in the ledge of the tray.

Referring now to FIGS. 1 through 3, a collection tray 10 according to the invention is a one-piece molded plastic member having a planar portion 12, a bowl-like or basin portion 14, and a live hinge 16 therebetween. The basin portion 14 is preferably provided with a bowl 17 having a central drain 18 which is provided with a sponge barrier 19. As shown, the sponge barrier is a diametrical member which reduces the area through which a sponge may pass. A sloped plateau, shelf or ledge 20 is formed between part of the bowl 17 and the hinge 16. Three slots 22, 24, 26 are provided in the ledge 20 for receiving an irrigation assembly as described in more detail below with reference to FIG. 6. A pair of substantially planar ears 28, 30 are provided on either side of the basin portion 14 adjacent to the hinge 16. Each ear is provided with a pair of holes 28a, 28b, 30a, 30b for receiving and holding instruments during a procedure.

According to the presently preferred embodiment, the outer edge 14a of the bowl or basin portion 14 is rolled down as shown in FIGS. 2 and 3. This provides a smooth periphery and adds structural support to the basin portion 14. The presently preferred embodiment of the collection tray 10 is designed to be used in conjunction with a surgical drape such as one of the drapes disclosed in U.S. Pat. Nos. 4,076,017, 4,105,019, and 4,149,537 to Haswell, the complete disclosure of which are hereby incorporated by reference herein in their entireties. For this purpose, the planar portion 12 of the tray is provided with two peel and stick adhesive pads 32, 34 and the proximal end of the basin portion 14 is provided with a peel and stick adhesive pad 36. These pads are used to affix the drape to the underside of the tray 10. When used in this manner, the fluids collected in the basin 14 are delivered through the drain 18 to the pocket formed by the drape.

Referring now to FIGS. 1 through 5, each of the slots 22, 24, 26 is substantially the same although angled differently relative to the hinge 16. Therefore, the geometry of the slots will be understood by describing one slot, 24 with reference to FIGS. 4 and 5. Slot 24 includes a relatively narrow and relatively deep groove 24a having a proximal end 24b and a distal end 24c. The distal end 24c is preferably angled as shown and described below with reference to FIG. 6. A relatively broad and relatively shallow tapering groove 24d is located above a proximal portion of the groove 24a. The broader groove 24d is delineated from the narrower groove 24a by a pair of lower steps 24e, 24f and a pair of distal shoulders 24g, 24h. The distal shoulders 24g, 24h are preferably angled and parallel to the distal end 24c of the groove 24a. The geometry of the slots will also be better understood with reference to FIG. 6 as described below.

Figure 6:
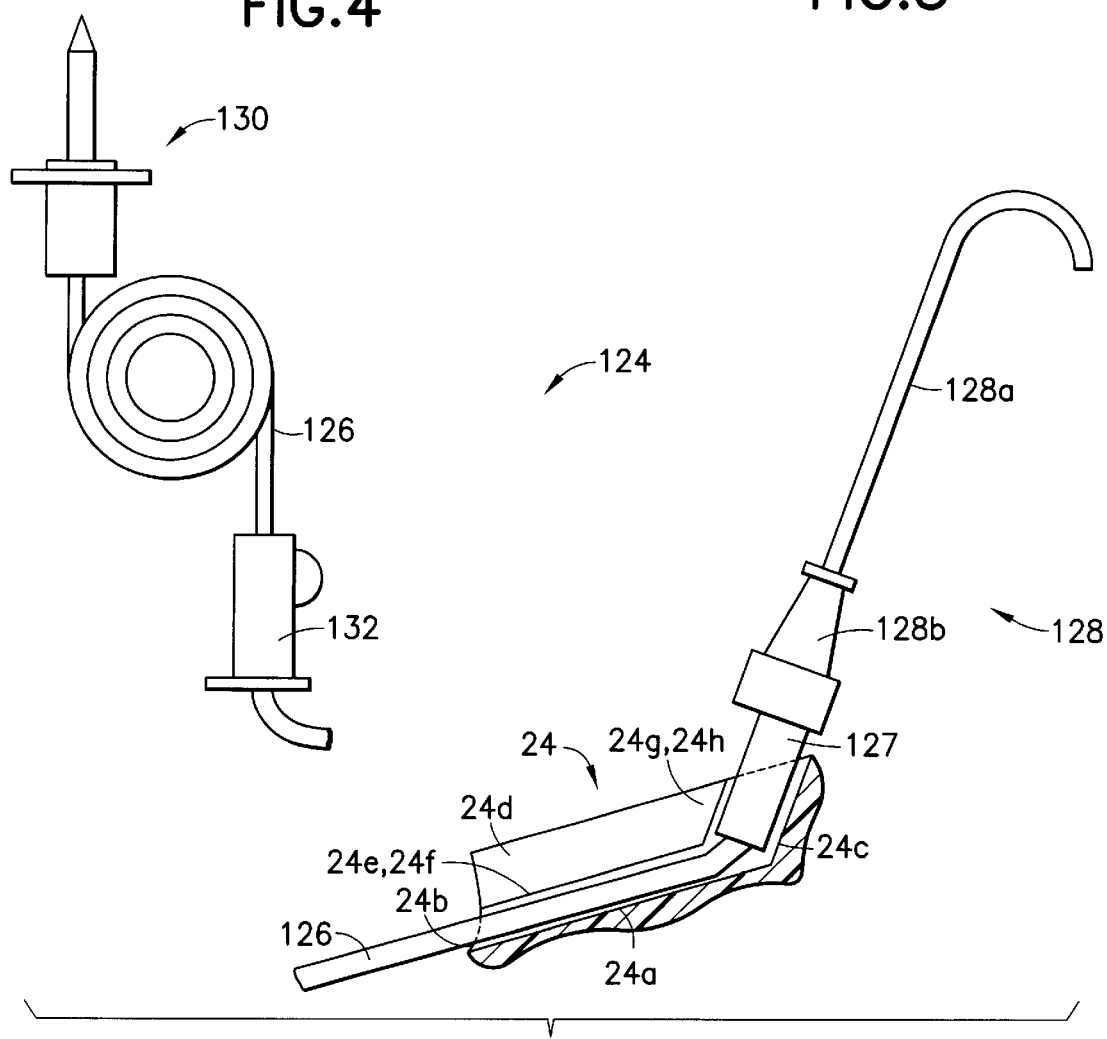
FIG. 6 is a broken schematic view of and irrigation fluid tube with an articulate nozzle assembly inserted into one of the slots of the ledge of the basin.

As mentioned above, the tray is intended to be used in conjunction with an irrigation system. Turning now to FIG. 6, an irrigation system 124 includes a medical grade tube 126 having an articulatable nozzle 128 at one end, a connection spike 130 at the other end, and a clip or roller valve 132 arranged on the tube at a convenient location. According to the present invention, the articulatable nozzle 128 includes a malleable annealed aluminum tube 128a which is insert molded in a plastic luer connector 128b. The nozzle 128 is coupled to the tube 126 by means of a mating luer connector 127 which is attached to the end of the tube 126.

Referring now to FIGS. 1–6, in use, the tray 10 is placed so that the planar portion 12 is positioned under the patient's buttocks (not shown) and above a surgical drape (not shown). The planar portion is affixed to the drape with the adhesive strips 32, 34; and the proximal portion of the drape is affixed to the proximal portion of the basin 14 with the adhesive strip 36. Prior to placement, however, it is preferred that the tray be folded at the live hinge 16 so that the basin portion 14 is angled down from the planar portion 12 as shown in FIG. 2. This provides a clear angle of view of the procedural site, enhances the position of the slots 22–26, and lowers the drain 18 so that collected fluids are readily drained from the basin 14. As shown in FIG. 2, the basin portion is folded (bent) approximately 20° relative to the planar portion. Bending a greater or lesser amount may be preferable for different procedures. It will be understood, however, that the live hinge portion of the tray should be constructed so that the basin portion can be bent and maintained over a large range relative to the planar portion (e.g., 0–60 degrees) and so that once bent, will maintain itself in a relatively stable angular position relative to the planar portion. When the tray 10 is so installed, the holes 28a, 28b, 30a, 30b in the ears 28, 30 are available and well placed to receive and hold instruments such as clamps, scissors, etc.

After the tray 10 is installed, the irrigation system 124 is deployed by connecting the spike 130 to a sterile water supply (not shown) and by inserting the nozzle assembly 128 in a selected one of the slots 22, 24, 26. As shown best in FIG. 6, the slot (e.g. 24) is dimensioned such that the luer connector 127 fits snugly in the space between the shoulders 24g, 24h and the distal end 24c of the groove 24a. The tube 126 lies in the deep groove 24a and is guided into the groove by the tapered groove 24d. The grooves are dimensioned relative to the tube 126 such that water flow through the tube is not impeded. With the tray and the irrigation system 124 so deployed, the practitioner can adjust the nozzle assembly 128 in several different ways. The assembly may be rotated about its longitudinal axis in the slot. The malleable portion 128a may be bent to various configurations. Moreover, the entire nozzle assembly 128 may be moved from one slot to another slot.

Those skilled in the art will appreciate that the tray 10 may be made to have different dimensions for different purposes. Small trays may be used for smaller patients and large trays may be used for larger patients. According to the presently preferred embodiment, a general purpose tray 10 is approximately fifteen to sixteen inches from side to side and approximately twelve inches from the proximal edge of the basin 14 to the distal edge of the planar portion 12. The deepest part of the basin 14 is approximately three and one half inches; and the rolled portion 14a is approximately 0.125 inches deep. The shelf 20 extends approximately three inches from the hinge 16 at its most proximal point and slopes down at an angle of approximately 20° relative to the planar portion 12 when the hinge 16 is not bent. The slots 22, 24, 26 in the shelf 20 are approximately one half inch deep and approximately one and one half inches long. It will be appreciated that the collection tray 10 provides a relatively large collection basin 14 which is easily positioned and easily drained. The tray 10 is easy to manufacture, easy to use, and does not interfere with the procedure. It will also be appreciated that sterile trays, packed in plastic bags can be stacked one inside another for economical shipment and storage. The inexpensive plastic trays are disposable and/or recyclable. The presently preferred material for manufacturing the tray is a medical grade gamma stable low density polyethylene such as PETG.

There have been described and illustrated herein a preferred embodiment of a collection tray for use in pelvic procedures. While a single preferred embodiment of the invention has been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while particular geometric shapes have been shown, it will be recognized that other similar shapes could be used with similar results obtained. Moreover, while particular configurations have been disclosed in reference to the slots for receiving the irrigation nozzle, it will be appreciated that other similar configurations could be used as well. Furthermore, while the basin has been disclosed as having a drain, it will be understood that given the relatively large size of the basin, a drain may be unnecessary for some procedures. Further yet, while a live hinge has been disclosed and is preferred, it will be appreciated that other types of hinges could be utilized. It will therefore be appreciated by those skilled in the art that yet other modifications could be made to the provided invention without deviating from its spirit and scope as so claimed.

I claim:

1. A collection tray for use in pelvic procedures, comprising:
    a single piece molded plastic tray having a planar portion, and a basin portion, said basin portion including a basin and a shelf located within said basin adjacent to said planar portion.
2. A collection tray according to claim 1, further comprising:
    a drain in said basin portion.
3. A collection tray according to claim 2, wherein:
    said drain includes a sponge barrier for preventing a sponge from passing through said drain.
4. A collection tray according to claim 1, wherein:
    said shelf includes at least one slot for holding an irrigation nozzle.
5. A collection tray according to claim 4, further comprising:
    a removable irrigation nozzle assembly dimensioned to fit snugly in said at least one slot.
6. A collection tray according to claim 5, wherein:
    said irrigation nozzle assembly includes a malleable nozzle.
7. A collection tray according to claim 6, wherein:
    said malleable nozzle is an annealed aluminum tube.
8. A collection tray according to claim 1, wherein:
    said shelf has a surface which is sloped.
9. A collection tray according to claim 1, wherein:
    said shelf includes at least one slot.
10. A collection tray according to claim 1, wherein:
    said plastic tray further includes at least one ear lying adjacent said basin portion and said planar portion, said ear defining at least one hole.
11. A collection tray according to claim 10, wherein:
    said at least one ear includes a pair of ears, each of said ears defining at least one hole.
12. A collection tray according to claim 1, wherein:
    said plastic tray further includes a live hinge lying between said planar portion and said basin portion.
13. A collection tray for use in pelvic procedures, comprising:
    a single piece molded plastic tray having a planar portion, and a basin portion, said basin portion including a basin, a drain located within said basin, and a shelf located within said basin between said drain and said planar portion.

14. A collection tray according to claim 13, wherein:
said shelf is inclined relative to said planar portion.

15. A collection tray according to claim 14, wherein:
said shelf includes means for holding an irrigation nozzle.

16. A collection tray according to claim 13, wherein:
said plastic tray further includes at least one ear lying adjacent said basin portion and said planar portion, said ear defining at least one hole.

* * * * *